United States Patent [19]

Kurek

[11] 4,448,994

[45] May 15, 1984

[54] REDUCTION OF C-NITROSOARYLAMINES

[75] Inventor: Paul R. Kurek, Schaumburg, Ill.

[73] Assignee: UOP Inc., Des Plaines, Ill.

[21] Appl. No.: 533,071

[22] Filed: Sep. 16, 1983

[51] Int. Cl.$^3$ .............................................. C07C 85/11
[52] U.S. Cl. ...................................... 564/416; 564/420
[58] Field of Search ................................ 564/416, 420

[56] References Cited

U.S. PATENT DOCUMENTS

| | | | |
|---|---|---|---|
| 1,948,330 | 2/1934 | Calvert | 564/416 |
| 2,495,774 | 1/1950 | Roberts | 564/416 X |
| 2,974,169 | 3/1961 | Newby et al. | 206/576 |
| 4,313,002 | 1/1981 | Symon et al. | 564/423 |

FOREIGN PATENT DOCUMENTS 155319  12/1920  United Kingdom ................ 556/416

*Primary Examiner*—Paul F. Shaver
*Attorney, Agent, or Firm*—James R. Hoatson, Jr.; Eugene I. Snyder; William H. Page, II

[57] ABSTRACT

Alkali metal salts of C-nitrosoarylamines may be readily reduced in aqueous solution by a reducing sugar. The reaction affords the corresponding aminoarylamine in good yield with little, if any, byproduct formation and affords a method of preparing aminoarylamines without isolation of the C-nitrosoarylamine.

8 Claims, No Drawings

REDUCTION OF C-NITROSOARYLAMINES

BACKGROUND OF THE INVENTION

P-aminodiphenylamines are widely used as intermediates in the manufacture of alkylated derivatives, which find broad utility as antiozonants and antioxidants. For example, alkylation of p-aminodiphenylamine (PADPA) with acetone provides the broadly used antiozonant N-phenyl-N'-isopropyl-p-phenylenediamine.

The most accessible route to p-aminodiphenylamines involves N-nitrosation of a diphenylamine, rearrangement of the resulting N-nitrosodiphenylamine (NNODPA) to the corresponding C-nitrosodiphenylamine, e.g., p-nitrosodiphenylamine (PNODPA), and subsequent hydrogenation of the latter to the p-aminodiphenylamine. It long has been known that the procedure is fraught with difficulties, some of which result from objectionable properties of p-nitrosodiphenylamine, which is representative of the class of C-nitrosodiphenylamines. In particular, the latter are carcinogens requiring extensive precautions in their handling, a problem compounded by the fact that p-nitrosodiphenylamine is often obtained as a light powder, easily dispersed and airborne. Another difficulty arises from the thermal instability of p-nitrosodiphenylamines, so that there is a tendency during their subsequent hydrogenation to form highly-colored byproducts which are difficult to remove from PADPA and which substantially reduce the commercial value of the latter material.

U.S. Pat. No. 2,974,169 describes the reduction of an aqueous solution of an alkali metal salt of PNODPA with palladium on charcoal. This method has the advantage of obviating, in large part, the formation of objectionable color bodies. However, catalytic reduction in aqueous media presents substantial disadvantages, and because the patentees contemplate isolation of PNODPA the necessity of handling carcinogens remains. These problems were addressed and overcome in U.S. Pat. No. 4,313,002, where the patentees' discovery of the solubility in particular organic solvents of some metal salts of p-nitrosodiphenylamines made possible the catalytic reduction of the latter in non-aqueous media without the necessity of isolating and handling the p-nitrosodiphenylamine.

SUMMARY OF THE INVENTION

The invention described herein offers an advantageous alternative to catalytic reduction of C-nitrosoarylamines. I have discovered that salts of the latter, which are readily formed in aqueous base, may be reduced by sugars. This is the basis of my invention, which is a method of preparing aminoarylamines by reducing an aqueous solution of an alkali metal salt of a C-nitrosoarylamine with a sugar and recovering the formed aminoarylamine.

DESCRIPTION OF THE INVENTION

Although many sugars long have been known to reduce various metals, such as silver and copper, they are not generally known to enter into oxidation-reduction reactions with other organic compounds. Therefore, it was particularly surprising to observe that reducing sugars enter into an oxidation-reduction reaction with salts of oximes which originate from C-nitrosoarylamines. The overall result of such a reaction is to reduce the nitroso group to an amino group in good yield with few, if any, byproducts and under relatively mild conditions. This observation leads to my invention, which is a method of making an aminoarylamine comprising contacting an aqueous basic solution of an alkali metal salt of a C-nitrosoarylamine with a reducing sugar, and recovering the aminoarylamine formed thereby.

The C-nitrosoarylamines which may be used in the practice of this invention have the formula,

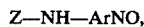

Z—NH—ArNO, where Ar is a divalent radical whose parent is an aromatic hydrocarbon or a substituted aromatic hydrocarbon and Z is an alkyl group or, more usually, a monovalent radical whose parent is an aromatic hydrocarbon or a substituted aromatic hydrocarbon. The aromatic hydrocarbon which may be the parent of either Ar or Z is most usually benzene, but may also be naphthalene, anthracene, phenanthrene, fluorene, and so forth. The parent aromatic hydrocarbon, especially when the parent is benzene, also may bear one or more substituents such as an alkyl, alkoxy, and halogen. When Z is not a monovalent radical whose parent is an aromatic hydrocarbon or a ring substituted aromatic hydrocarbon it is an alkyl group, such as methyl, ethyl, propyl, butyl, pentyl, hexyl, decyl, undecyl, dodecyl, hexadecyl, heptadecyl, octadecyl, and so forth.

4-Nitrosodiphenylamine is the premier example of the class of C-nitrosoarylamines which may be used in this invention because of its relative importance. However, examples of other C-nitrosoarylamines which may be used include 4-nitrosophenylmethylamine, 4-nitrosophenylethylamine, 4-nitrosophenylpropylamine, 4-nitrosophenylbutylamine, nitrosonaphthalenylhexylamine, nitrosoanthracenyloctylamine, 4-nitroso-3'-chlorodiphenylamine, 4-nitroso-3'-bromodiphenylamine, 4-nitroso-3'-fluorodiphenylamine, 4-nitroso-2'-methoxydiphenylamine, 4-nitroso-3'-butoxydiphenylamine, 4-nitroso-2-methyl-4'-butyldiphenylamine, 4-nitroso-3-chloro-2'-nonyloxydiphenylamine, 4-nitroso-2-methoxy-3'-pentyldiphenylamine, and 4-nitroso-2-butoxy-3'-chlorodiphenylamine.

The C-nitrosoarylamine is then converted to its alkali metal salt. The C-nitrosoarylamines of this invention form oxime salts in basic solutions according to the reaction, using 4-nitrosodiphenylamine as an example,

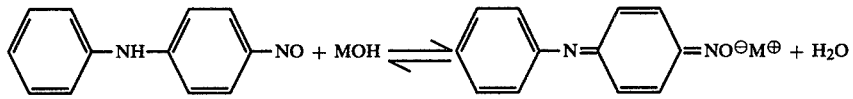

where M is an alkali metal. The conversion to alkali metal salts most often is brought about using alkali metal hydroxides as the base. However, other bases, such as carbonates, may be used. Alkali metal salts are preferred because of their solubility in water, with the sodium and potassium salt generally being employed.

The aqueous basic solution of an alkali metal C-nitrosoarylamine is then contacted with a reducing sugar. The sugars which may be used in the practice of this invention are either a monosaccharide or a disaccharide, both of which are examples of carbohydrates. Carbohydrates are polyhdroxyaldehydes, polyhydroxyketones, or compounds that can be hydrolyzed to them. A carbohydrate that cannot be hydrolyzed to simpler compounds is called a monosaccharide; one that can be hydrolyzed to two monosaccharide molecules is called a disaccharide. A monosaccharide may be classified according to the number of carbon atoms it contains; a hexose is a six-carbon monosaccharide, a pentose is a five-carbon monosaccharide, and a tetrose is a four-carbon monosaccharide. Carbohydrates that reduce basic solutions of copper (II) (Fehling's or Benedict's reagent) or an ammoniacal solution of silver (Tollens' reagent) are known as reducing sugars. All monosaccharides, whether aldose or ketose, are reducing sugars. Most disaccharides are reducing sugars with sucrose, or common table sugar, being a notable exception. Among the monosaccharides which may be used in the practice of this invention the hexoses are preferred to the pentoses and tetroses because of the former's greater availability. Among the hexoses which may be employed are included glucose, mannose, fructose, galactose, talose, allose, altrose, and idose, with glucose being the monosaccharide of choice. The amount of reducing sugar used is not critical so long as a sufficient quantity is employed to supply the requisite number of hydrogens for the reduction of the C-nitroso group to an amino group. Generally at least one molar proportion of reducing sugar, based on C-nitrosoarylamine, is used with amounts up to about four molar proportions sometimes being employed. Although greater proportions of reducing sugar are not deleterious they also are generally not beneficial.

Contacting the aqueous basic solution of an alkali metal salt of a C-nitrosoarylamine with a reducing sugar may be performed at a temperature up to that of reflux of the solution, which may be as high as about 110° C., although reaction occurs even at temperatures as low as about 40° C. It is found most convenient to work at a temperature between about 70° and 100° C. since an elevated temperature provides the advantages of reduced viscosity, increased solubility of the salt, and an increased reaction rate.

The practice of this invention can be readily exemplified using 4-nitrosodiphenylamine. The amine is converted to its alkali metal salt using an excess of a solution of an alkali metal hydroxide, such as sodium hydroxide or potassium hydroxide. The solution of the alkali metal salt of the C-nitrososarylamine then is heated to a temperature between about 70° and about 100° C. To this heated solution is added, with stirring the reducing sugar at such a rate that the resulting exotherm maintains the temperature within the stated range. Stirring is continued for about an hour after the reaction exotherm subsides after which the mixture is cooled to room temperature. The formed aminodiarylamine is then recovered by suitable means. Often this can be accomplished merely by collecting the solids, as by filtration, and washing them well with water. Alternatively, the mixture can be extracted with an organic solvent and the aminoarylamine recovered from the organic solvent by suitable means, as by evaporation of the solvent, with or without subsequent further purification of the aminoarylamine, as by recrystallization.

The examples given below are for illustrative purposes only and are not intended to limit the invention thereto.

EXAMPLE I

To a one liter, three-necked flask equipped with a mechanical stirrer and thermometer was added 20 g (0.1 mol) 4-nitrosodiphenylamine and a solution of 10 g (0.25 mol) sodium hydroxide in 100 ml of water. The mixture was stirred until the organic material was completely dissolved. To a 250 ml Erlenmeyer flask fitted with gooch tubing was charged 40 g (0.22 mol) glucose with the other end of the tubing attached to the reaction flask. The mixture was heated with stirring to 80° C., at which point heating was discontinued, and glucose was added slowly from the Erlenmeyer flask over a one-half hour period while maintaining a temperature of approximately 80° C. via the reaction exotherm. Stirring was continued for one hour after addition of glucose was complete, whereupon the reaction mixture was cooled to room temperature. The cooled mixture was extracted with 200 ml of ether, the ether layer was separated and dried, after which ether was removed by evaporation. Analysis of the solid residue by high pressure liquid chromatography showed 4-aminodiphenylamine was formed in 92% yield.

EXAMPLE 2

A reaction mixture of 34 g (0.17 mol) 4-nitrosodiphenylamine and 30 g (0.75 mol) sodium hydroxide in 120 ml water was prepared as described above and reduction carried out by the addition of 23 g (0.13 mol) glucose. After the reaction mixture was cooled the solid was collected by filtration, washed with copious amounts of water, then dried. Analysis by high pressure liquid chromatography of the collected solid showed that the product, 4-aminodiphenylamine, was formed in 70% yield.

What is claimed is:

1. A method of making an aminoarylamine comprising contacting an aqueous basic solution of an alkali metal salt of a C-nitrosoarylamine with a reducing sugar at a temperature from about 40° C. to about 110° C., and recovering the aminoarylamine formed thereby.

2. The method of claim 1 where the C-nitrosoarylamine is a C-nitrosodiarylamine.

3. The method of claim 2 where the C-nitrosodiarylamine is 4-nitrosodiphenylamine.

4. The method of claim 1 where the sugar is a monosaccharide.

5. The method of claim 4 where the sugar is a hexose.

6. The method of claim 5 where the hexose is glucose.

7. The method of claim 1 where the sugar is a disaccharide.

8. The method of claim 1 where the temperature is from about 70° to about 100° C.

* * * * *